United States Patent [19]

Spence et al.

[11] Patent Number: 5,219,099
[45] Date of Patent: Jun. 15, 1993

[54] COAXIAL LEAD SCREW DRIVE SYRINGE PUMP

[75] Inventors: Charles F. Spence; Steven M. Clark, both of Pasadena, Calif.

[73] Assignee: California Institute of Technology, Pasadena, Calif.

[21] Appl. No.: 755,804

[22] Filed: Sep. 6, 1991

[51] Int. Cl.⁵ .............................................. G01F 11/06
[52] U.S. Cl. .................................. 222/325; 222/333; 222/390; 604/155
[58] Field of Search ........................ 222/325, 333, 390; 604/154, 155, 156, 211

[56] References Cited

U.S. PATENT DOCUMENTS

| | | | |
|---|---|---|---|
| 2,498,672 | 2/1950 | Glass | 604/155 |
| 2,627,270 | 2/1933 | Glass | 604/155 |
| 3,336,925 | 8/1967 | Thompson III | 222/333 X |
| 3,390,815 | 7/1968 | Kavan et al. | 222/333 X |
| 3,425,416 | 2/1969 | Loughry | 604/155 |
| 3,674,009 | 7/1972 | Williamson | 604/155 X |
| 3,799,406 | 3/1974 | St. John et al. | 604/211 X |
| 4,335,834 | 6/1982 | Zepkin | 222/390 X |
| 4,731,058 | 3/1988 | Doan | 604/155 |
| 4,769,009 | 9/1988 | Dykstra | 222/390 |
| 4,848,606 | 7/1989 | Taguchi et al. | 222/333 |

FOREIGN PATENT DOCUMENTS 1465653  1/1967  France ............................ 604/155

OTHER PUBLICATIONS

Materials and Processes in Manufacturing, fifth edition E. Paul DeGarmo, P. E. Macmillan Publishing copyright 1979.
IBM Technical Disclosure Bulletin Paste dispenser, vol. 16, No. 7, Dec. 1973.

Primary Examiner—Andres Kashnikow
Assistant Examiner—Kenneth Bomberg
Attorney, Agent, or Firm—Leonard Tachner

[57] ABSTRACT

A syringe pump, uses a stepping motor to rotate a lead screw with precision and in turn advance a zero-backlash ball nut or vice-versa to drive the syringe plunger. This invention is designed to eliminate virtually all forces that are not coaxially aligned with the plunger's axis by utilizing a drive shaft kinematically supported on a reference member. The barrel of the syringe is kinematically supported on the reference member with its axis aligned with the axis of the drive shaft. The drive shaft is advanced by the ball nut and drive shaft assembly to drive the plunger which is kinematically supported at one end by the end of the drive shaft and at the other end by the internal wall of the barrel.

12 Claims, 3 Drawing Sheets

COAXIAL LEAD SCREW DRIVE SYRINGE PUMP

FIELD OF THE INVENTION

The invention relates to a high resolution. precision, syringe pump designed to eliminate all forces not aligned with the axis of the plunger, thus keeping the motion smooth and repeatable with precision.

BACKGROUND ART

The need for more precise delivery mechanisms for analytical chemistry techniques is increasing. Potentially, syringe pumps offer the resolution and dynamic range of an analytical balance for the delivery of liquid reagents. Unfortunately, prior-art syringe pump designs do not achieve this precision, resolution and dynamic range.

Most syringe pumps use a stepping motor to turn a lead screw or its mating nut to drive the syringe plunger. The lead screw/stepping motor combination allows for a simple, digitally-controlled open-loop plunger drive mechanism having a resolution defined by the number of steps per revolution of the stepping motor and the pitch of the lead screw. By simple calculation it can be determined that a linear resolution as fine as 94 nm per step can be achieved with a lead screw pitch of 1.2 mm per revolution and a a micro-stepping motor having 12,800 steps per revolution. A mechanism of this type driving the plunger of a 5 ml Hamilton Gastight syringe, can theoretically achieve a liquid delivery resolution of 10 nl. Current syringe pump designs compromise the precision and repeatability of this resolution in their mechanical architecture and layout.

Many syringe pumps have the axis of the lead screw offset from the axis of the syringe plunger. Such an offset drive may cause flexing of links that connect the plunger to the lead screw, warping of the plunger itself and/or warping of the syringe barrel, resulting in inaccurate deliveries and leakage. These designs also have substantial hysteresis, making them unusable for precision infusion/extraction applications.

Some designs have the lead screw axis aligned with the axis of the syringe plunger, turning either the screw or the nut through a gear train. Gear trains are used to increase drive torque to compensate for smaller motors. They also allow for the use of an off-axis motor creating a more compact design, and they increase the effective resolution of a low resolution stepping motor. Although the problem of backlash of gear trains can be eliminated, gear trains introduce additional errors to the motion of the plunger and add complexity to the overall mechanical design. Other designs have the lead screw axis offset from the axis of the syringe plunger and use a gear train to couple the lead screw drive to the plunger, which necessarily compromises accuracy.

The principal objectives of this invention are:
1. To provide a coaxially driven syringe pump with all forces aligned with the plunger's axis of motion. The essential elements that are axially aligned are the syringe barrel, the syringe plunger, the means for coupling axial motion of a lead-screw drive mechanism to the syringe plunger, the axis of the lead screw/nut assembly and the drive motor (preferably a stepping motor).
2. To provide a highly repeatable drive mechanism. A repeatable system can be calibrated and made highly accurate.
3. To allow for misalignment of elements due to errors in manufacturing and/or assembly and still provide high repeatability.

In the preferred embodiment of this invention, the errors are limited to the precision of the drive motor (which may be a servo or other motor, preferably a stepping motor), the precision of the lead screw, the thermal expansion coefficients of the mechanical components and the thermal expansion coefficients of the liquid being pumped. Any error due to compressibility of the materials used for the drive system should be several orders of magnitude less than the combination of the above factors. Only the compressibility of the plunger head in the syringe barrel is of any significance because it necessarily includes at least one ring of compliant material for sealing between the plunger and the wall of the syringe barrel. By limiting the errors of the mechanism to those previously described, a simple open loop control system can use a stepping motor to obtain highly accurate results.

A rigid body has six independent degrees of freedom for motion. They are translational motion along three orthogonal axes and rotational motion about each of the three orthogonal axes. The definition of "kinematic support" requires that, for every degree of freedom to be constrained between two bodies, there be only one point of contact between them. If more than one point of contact exists per degree of freedom, the system is said to be degenerate. In a semikinematic design, a point contact may be expanded to a surface in order to bear a larger load, provided that the contact may nevertheless be theoretically reduced to a point. However, where a semikinematic coupling is used, it is necessary that the contacting surfaces be "run in" to insure proper alignment by operating the coupled mechanism through its full range of expected motion a sufficient number of times for the parts in contact to wear off "high spots" on the contacting surfaces before final instrument alignment. Thus, through kinematic design or at least semikinematic design, repeatable motion can be achieved with precision without relying on precision manufacture of the parts. If the motion is repeatable, it can be measured and calibrated and thus made highly accurate.

SUMMARY OF THE INVENTION

Although several preferred embodiments of the invention are illustrated and described, it will be recognized that modifications and equivalents may readily occur to those skilled in the art. In each embodiment, a syringe pump is driven by precision means, preferably a stepping motor and a coaxial lead screw or the equivalent. The essential elements of the syringe pump are provided with means for kinematic support where the term "kinematic" as used hereinafter is defined to include "semikinematic." The elements of the syringe pump are: A syringe barrel with means for providing kinematic support for the syringe barrel, a syringe plunger, a plunger drive means, a kinematic coupling means which connects the drive means to the plunger, a lead screw (preferably a ball screw), a nut (preferably a ball nut), a drive motor, a rigid mount for the motor, a coupling for connecting the motor to rotate either the lead screw or the nut and a reference member supporting all of the above with the kinematic coupling means connecting the drive means between the drive motor and plunger in coaxial alignment with the plunger.

There are two embodiments described herein for supporting the syringe barrel. In one such embodiment, the syringe barrel is supported by two pairs of rigid balls spaced apart and affixed to a block on the reference member (such as a support plate or cylinder). These balls constrain rotational and translational motion about two axes perpendicular to the barrel axis. A flange at one end of the barrel is seated against the block to constrain translational motion along the barrel axis in one direction. A spring-loaded clamp affixed to the block for holding the flange against the block may be provided to constrain translational motion along the axis of the barrel in the opposite direction. In the case of a syringe pump used only for infusion or only for extraction, constraint of the translational motion of the barrel in only one direction may be sufficient. The barrel is constrained from rotating about its axis by friction; it is not, however, kinematically constrained from rotation. A pin may be added to kinematically restrain the rotation of the barrel along its axis, but clamping means would still be necessary to overcome any off-axis forces due to errors in the alignment of the drive components. This pin would also kinematically define the position of the barrel on the reference member. This would assure the utmost in repeatability for a calibrated system, but would be suitable for only a single syringe barrel/plunger combination. It should be mentioned that even though the barrel flange rests against a flat surface, normally there will be only one point of contact due to irregularities in the flange of a typical glass syringe. Thus, the flange and a pin used to constrain the barrel from rotation provide a point contact.

In a second embodiment for supporting the syringe barrel, the barrel is provided with kinematic support by a gimbal mount which provides constraint against translational motion in either direction along the barrel's axis and against rotation along the barrel axis. The flange of the barrel is rigidly attached such as by clamping to the rear ring of the gimbal mount. The rear ring is supported by a front ring through two balls, one on each side of center, seated in facing V grooves which are machined along the diameter of the front and rear rings. The rings are held together against the two balls by resilient means, such as springs, at the outer ends of the V grooves. The front ring is provided with two opposite V-grooved radial arms. These arms, separated by two balls, are resiliently held against two mating V-grooved support blocks which are rigidly attached to the reference member.

When a drive motor and lead screw are employed as precision means for driving a syringe plunger using an axial drive shaft, the drive shaft may be made hollow to allow the drive shaft to be moved with precision over the lead screw by a nut as the lead screw is rotated with precision by the rigidly mounted drive motor. Alternatively, the drive motor may have a hollow shaft for the lead screw to pass through it. In this case the nut is turned with precision by the rigidly mounted drive motor, thus moving the lead screw with precision. In either case, the lead screw's motion is coupled to the driven end of the plunger by a ball centered at the end of the lead screw and affixed thereto. That ball centers itself in a trihedral hollow or conical recess centered at the driven end of the plunger. The lead screw is prevented from rotating while driving the plunger into the syringe barrel by an arm affixed perpendicularly to the lead screw and riding on a precision surface such as a rod or a ground surface plate parallel to the lead screw. The arm is held against the surface plate or rod by a spring-loaded clamp. In cases where the drive motor and lead screw withdraw the plunger from the syringe barrel, a collar may be provided on the driven end of the coupler with clamping means affixed to the lead screw extending over the collar of the plunger. Resilient means is provided between the collar and the clamping means. When the plunger is coupled to the lead screw in this manner, the syringe barrel is held on the reference member by the four-ball arrangement referred to above. Alternatively, the plunger may be rigidly attached to the lead screw, in which case the syringe barrel would be held in the gimbal mount. The drive motor is provided with bearings for the motor's drive shaft to restrain the drive shaft from translation along its axis.

In the embodiments which use a hollow drive shaft, the shaft is kinematically supported on the reference member in a manner similar to the four-ball kinematic support of the syringe barrel, but in this case using a perpendicular pin secured in the support member to prevent the hollow drive shaft from turning on its axis. The pin extends into a longitudinal slot in the drive shaft and thus prevents the hollow drive shaft from rotating on its axis as it advances or retracts to drive the plunger in or out of the syringe barrel. That pin secured in the support member is fully equivalent to an arm extending perpendicularly to the hollow drive shaft and riding on a precision surface such as a rod or a ground surface plate parallel to the drive shaft. A spring-loaded clamping means may be provided to keep the arm against the precision surface. The plunger is then coupled to the drive shaft using the ball point technique describe above or is rigidly attached. The syringe barrel is mounted in one of the two alternative ways described as dictated by the plunger coupling technique.

DESCRIPTION OF A PREFERRED EMBODIMENT

Figure 1:
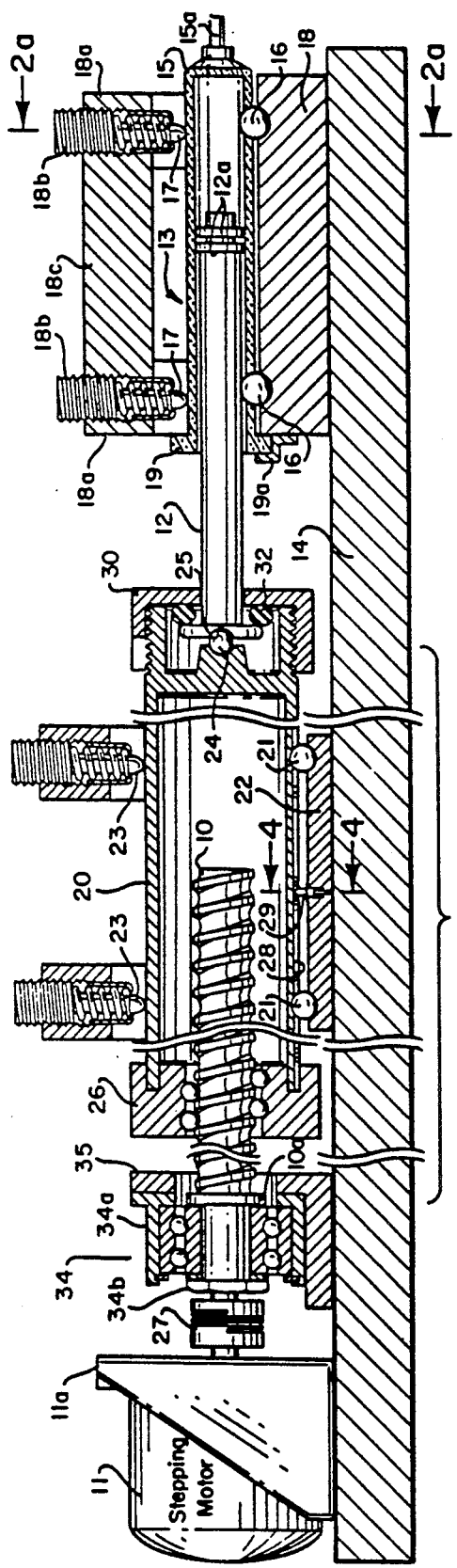
FIG. 1 is a longitudinal section taken along the axis of a syringe pump having a coaxial lead screw drive embodying the present invention.

Referring to FIG. 1, a lead screw 10 turned by a stepping motor 11 drives a plunger 12 of a syringe 13, such as a 5 ml syringe of the Hamilton type shown in U.S. Pat. No. 3,150,801. It will be appreciated that different types of syringes may be employed for different applications. A hollow drive shaft 20 is advanced and retracted by the lead screw 10 through a zero-backlash ball nut 26 to avoid hysteresis. The barrel 15 is kinematically supported on a reference member 14, which may be a metal plate. In theory, the reference member may have any suitable form that provides a rigid reference in coaxially aligning the hollow drive shaft 20 and the syringe barrel 15 to eliminate all forces of motion not aligned with the axis of the syringe barrel 15 and plunger 12. Thus for example, the entire assembly could be mounted within a hollow-cylinder.

Figure 2B:
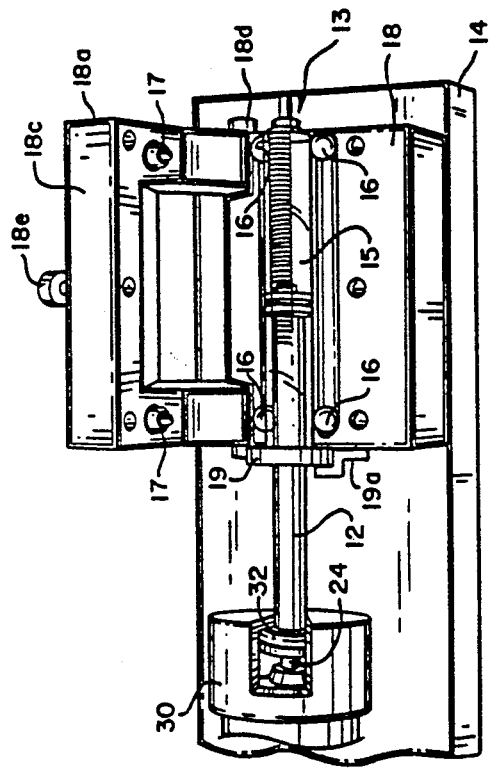
FIG. 2b illustrates in an isometric view the yoke of resilient clamping means pivoted out of the way to remove and replace a syringe.
Figure 2A:
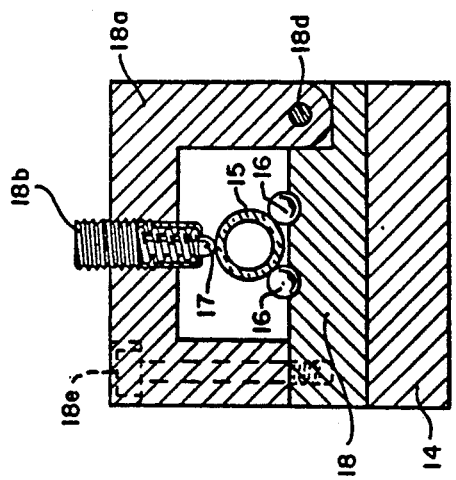
FIG. 2a is a transverse section taken along a line 2a—2a in FIG. 1.

The syringe barrel 15 is kinematically supported at two places along its length. The support at each place is comprised of two balls 16 fixed on the reference member 14 by a spacing block 18 as shown in FIG. 2a in a transverse cross-section taken along a line 2a—2a in FIG. 1. Resilient clamping means for holding the syringe barrel 15 in contact with the balls 16 is provided by two overhead spring-loaded ball pins 17 positioned directly over and perpendicular to the axis of the barrel.

In practice, the spacing block 18 is machined with precision for positioning the fixed balls 16 on the reference member 14. Then the spacing block 18 is positioned on the reference member 14. This allows for some adjustment of the position of the kinematic barrel support in making axial alignment of the syringe pump elements. The spacing block 18 also allows for making simple conversion for different size syringe barrels.

A yoke 18a, which extends from the spacing block 18 over the syringe barrel 15, as more clearly shown in FIG. 2a, carries the spring-loaded ball pins 17 directly over the axis of the barrel 15 centered between the two pairs of fixed balls 16. To adjust the loading on the spring for the ball pin 17, a cup is fitted into a smaller diameter portion of a threaded hole in the yoke 18a to hold the spring and ball pin. As set screw 18b is threaded further into the hole, the spring loading on the ball pin is increased. Cylindrical portions of the ball pins 17 maintain the alignment of the downward force perpendicular to and directly over the barrel axis, thus providing a resilient force to keep the barrel seated on the two pairs of fixed balls 16. Note that the yoke 18a at each end of the support is tied with the other end by a longitudinal member 18c on each side of the barrel and that both ends are secured to the spacing block 18 along one side by a hinge pin 18d and along the other side by a bolt 18e. This facilitates pivoting the yokes out of the way to place, replace or remove a syringe on the fixed balls 16, as shown in FIG. 2a.

The fixed balls 16 are shown seated in recesses in the spacing block 18 and should be cemented, welded or otherwise secured in place. However, in practice the balls 16 are preferably first aligned on top of cylindrical pins of the same diameter and fused in place onto the tops of the pins by high pressure. These pins are then press fit into properly aligned and spaced holes drilled into the spacing block 18. Both parts of this two-step process may be separately carried out with precision, thus providing for precision in the fabrication of the spacing block 18 with the pairs of balls. Suitable balls 16 may be obtained from Jergens, Inc. of Cleveland, Ohio.

Motion along the axis of the barrel 15 is constrained in one direction by a flange 19 bearing against a vertical surface of the spacing block 18. A similar flange or equivalent may be provided at the opposite end of the barrel to prevent motion in the opposite direction, but in practice a resilient spring clip 19a over the flange 19 may be secured to the spacing block.

The syringe plunger 12 is driven in line with the axis of the barrel 15 by a hollow drive shaft 20. The drive shaft is axially aligned with the syringe barrel 15 by kinematic support at two places along its length using at each place a pair of balls 21 affixed on a spacing block 22 and overhead spring-loaded ball pins 23 similar to the kinematic support described above for the barrel 15. The only difference in kinematic support is that for the drive shaft 20 the yokes are separate and permanently bolted to the spacing block 22 on both sides. Once the spacing blocks 18 and 22 are placed on the support member and are properly aligned on the reference member 14 by adjustment of the spacing block 18, coaxial alignment of the drive shaft 20 with the syringe barrel 15 is virtually assured during repeated operation. Note that the plunger 12 kinematically supported by the drive shaft at one end and by the syringe barrel 15 at the other end is thus properly aligned with its axis coaxial with the axis of the drive shaft 20 and the syringe barrel 15. The kinematic support of the syringe plunger 12 will now be described.

The drive shaft 20 drives the flanged end of the plunger 12 through a fixed thrust ball 24 that is centered on its axis and that fits in a trihedral hollow (a shallow conical depression) 25 centered on the axis of the plunger 12 during operation. Although this trihedral hollow is shown machined in the flanged end of the plunger, in practice it may be machined in a stainless steel button with a center pin that is then press fit into a hole drilled into the end of the plunger on its axis. The fixed thrust ball 24 may be held on the end of the drive shaft by any means suitable for restraining its motion such as a socket that encompasses just more than half of the ball to hold it in place, much like the ball is held at the end of a ball point pen. Because it need not roll, the fixed thrust ball 24 may be rigidly attached. It need only assist in maintaining the plunger 12 coaxially aligned with the drive shaft 20. The end of the plunger opposite the fixed thrust ball 24 is supported by the inside wall of the syringe barrel 15 through tandem compliant flanges 12a on the head of the plunger. The plunger 12 is thus kinematically supported at two places along its length.

Figure 3:
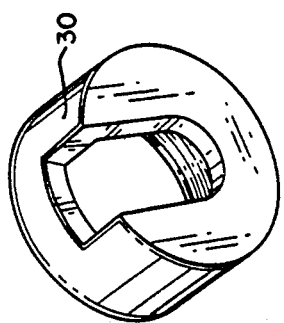
FIG. 3 illustrates in a perspective view a clamping cup used for securing the ball end of a drive shaft (in the embodiment of FIGS. 1 and 6) or lead screw (in the embodiment of FIG. 7) in abutment with a conical recess in the end of a syringe plunger.

The syringe plunger 12 is constrained against rotation by the friction of coupling means between the drive shaft and the plunger comprised of a cap 30 (shown in a perspective view in FIG. 3) fitted over a flange 31 and threaded on the end of the drive shaft 20 to hold both the drive shaft and the plunger in contact with the thrust ball 24. The rotational position of the barrel 15 may be defined by a slot provided in the flange 19 of the barrel and the resilient syringe clip 19a received in the slot and secured to the side of the spacing block 18. The syringe barrel 15 is constrained against rotation about its axis by friction between the fixed balls 16, the spring-loaded pins 17 and the outer surface of the syringe barrel. Compliant means, such as a rubber O-ring 32 between the flange 31 and the cup 30, holds the trihedral hollow 25 against the fixed thrust ball 24. The compliant flange 12a on the head of the plunger, such as a flange on a Teflon head, supports the head end of the plunger 12 in the syringe barrel 15.

The end of the drive shaft 20 opposite the syringe plunger 12 is coupled to the lead screw 10 by a zero-backlash ball nut 26. The lead screw 10 and a ball nut 26 are preferably of the type commercially available as a pair, such as the Beaver precision ball nut and lead screw manufactured by Dana, a subsidiary of Warner Electric Brake and Clutch Company. That type is preferred because its controlled backlash may be reduced to zero by preloading while maintaining smooth operation and high loading capability, although other techniques for zero-backlash preloading are known. As the ball nut 26 is advanced or retracted by turning the stepping motor 11 to rotate the lead screw 10 in one direction or the other, the lead screw passes into or out of the hollow shaft 20.

The lead screw 10 is coupled to the stepping motor 11 by a flexible coupling 27, preferably of the type manufactured by Rocom Corporation having two sets of three overlapping curved beams for transmitting torque in both directions but with zero-backlash. The stepping motor is rigidly affixed to the reference member 14 by a bracket 11a. The flexible coupling 27 thus allows smooth zero-backlash rotation in either direction. However, since the flexible coupling 27 has resilience along its axis, it is necessary to support the drive end of the lead screw 10 with a zero-backlash ball bearing assembly 34 press fit into a bracket 34a which is, in turn, secured to a bracket 35 by screws on flanges of the bracket 34a (not shown) and held against the bracket 35 by a lock nut 34b. The bracket 35 is secured on the reference member 14 in alignment with spacing blocks 22 and 18.

The thrust bearing 34 is preferably secured to the bracket 35 by screws so that the screws may be loosened while the stepping motor slowly rotates the lead screw back and forth after the drive shaft 20 and syringe barrel 15 have been coaxially aligned. This allows the thrust bearing 34 to adjust in position coaxially with the drive shaft 20 and syringe barrel 15. Once the thrust bearing 34 is thus aligned, the screws securing it to the bracket 35 are progressively tightened. Alternatively, the thrust bearing 34 may be press fit into or made with the outer race integral with the bracket 35 and the bracket 35 similarly aligned. However, it would be more complex to provide for both vertical and horizontal position adjustment of the bracket 35 than to provide the separate bracket 34a with screws through flanges. The holes for the screws are made oversize to allow the bracket 34a holding the thrust bearing 34 to self-adjust its position on the fixed bracket 35.

It should be noted that the lead screw has a collar 10a on the side of the thrust bearing 34 opposite the lock nut 34a. Pressing the inner race of the thrust bearing 34 against the collar 10a with the nut 34a, locks the inner race to the lead screw while the outer race is held rigidly in space by the brackets 34a and 35. This allows the lead screw 10 to be turned on its axis, while preventing it from moving along its axis in either direction relative to the stepping motor 11 secured in place by a bracket 11a. The flexible coupling 27 then serves to allow only slight deviation from coaxial alignment of the motor 11 and the lead screw 10.

Figure 4:
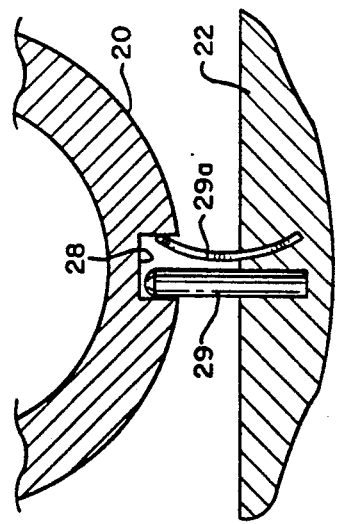
FIG. 4 is a cross section taken along a line 4—4 in FIGS. 1 and 6.

A longitudinal square groove 28 on the outside of the hollow cylindrical drive shaft 20 receives a pin 29 rigidly supported by the spacing block 22 in a fixed position directly under the axis of the drive shaft 20, as more clearly shown in cross-section in FIG. 4. This prevents the drive shaft from rotating as the lead screw 10 is rotated.

Referring to FIG. 4, the square groove 28 is wider than the diameter of the pin 29, but a leaf spring 29a secured in the block 22 bears against the side of the square groove to maintain the pin 29 against the other side of the groove. The hollow drive shaft 20 is thus kinematically supported and coaxially aligned with the axis of the syringe barrel which is, in turn, also kinematically supported and coaxially aligned with the syringe barrel.

Figure 5:
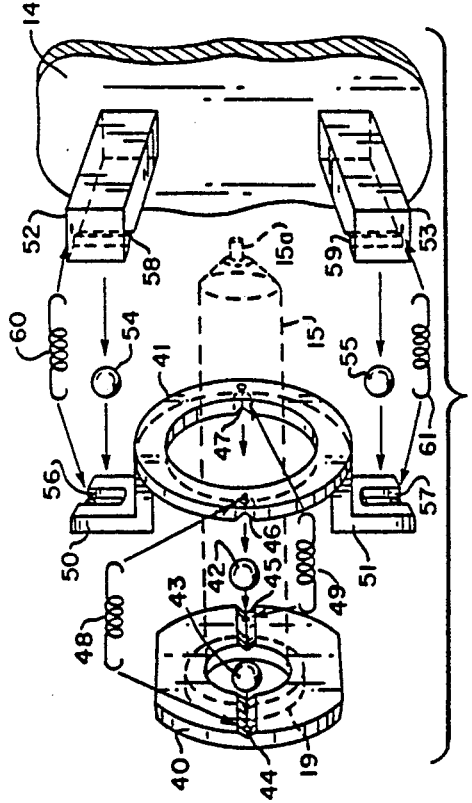
FIG. 5 illustrates a gimbal mount for an alternative kinematic support of the syringe barrel.

FIG. 5 illustrates a variation of the embodiment in FIG. 1 that provides a gimbal mount for the syringe barrel 15. It is shown in dotted lines in the position in which it is held by a rear ring 40 coupled to a front ring 41 through two bearing balls 42, 43 held in V grooves 44 through 47 machined in opposing faces of the rear and front rings 40 and 41. Springs 48 and 49 hold the two rings against the two balls in the opposing V grooves.

The flange 19 of the syringe barrel abuts the rear ring 40 to prevent it from moving forward as the syringe plunger is driven into the barrel. The syringe barrel is rigidly attached to the rear ring by either clamping or gluing the flange of the syringe barrel to the rear ring. The gimbal mount assembly is supported on a reference member through offset radial brackets 50, 51 by blocks 52 and 53 using bearing balls 54 and 55 in radial V grooves 56 through 59. Springs 60 and 61 hold the brackets 50 and 51 against the two balls 54 and 55 in the opposing V grooves. The spring provides sufficient tension to counteract any withdrawal forces expected for a given application.

It should be noted that the reference member may be the plate 14 of the embodiment shown in FIG. 1 and that the reference plane of that plate may be parallel to a plane passing through the grooves 58 and 59 and the grooves 56 and 57. In that case, the blocks 52 and 53 are extended to support the gimbal mount assembly away from the reference member.

A gimbal mount is desired when the plunger 12 is rigidly attached to the drive shaft, i.e., when the coupling mechanism of FIG. 1 comprised of elements 24, 25, 30 and 32 is not used. A rigid attachment may be desired to make the drive shaft 20 effectively function as the plunger. The gimbal mount allows for misalignment between the syringe barrel and the rigidly attached plunger. The barrel will center its axis with the axis of the plunger. An advantage of the gimbal mount is a more compact design. A disadvantage is the need to use a specially designed syringe plunger instead of any of the many syringe plungers commercially available. Another disadvantage is that it is not suitable for high pressure applications unless the gimbal assembly is made with substantially large and rigid components to avoid hysteresis under high pressure operation of the syringe.

Figure 6:
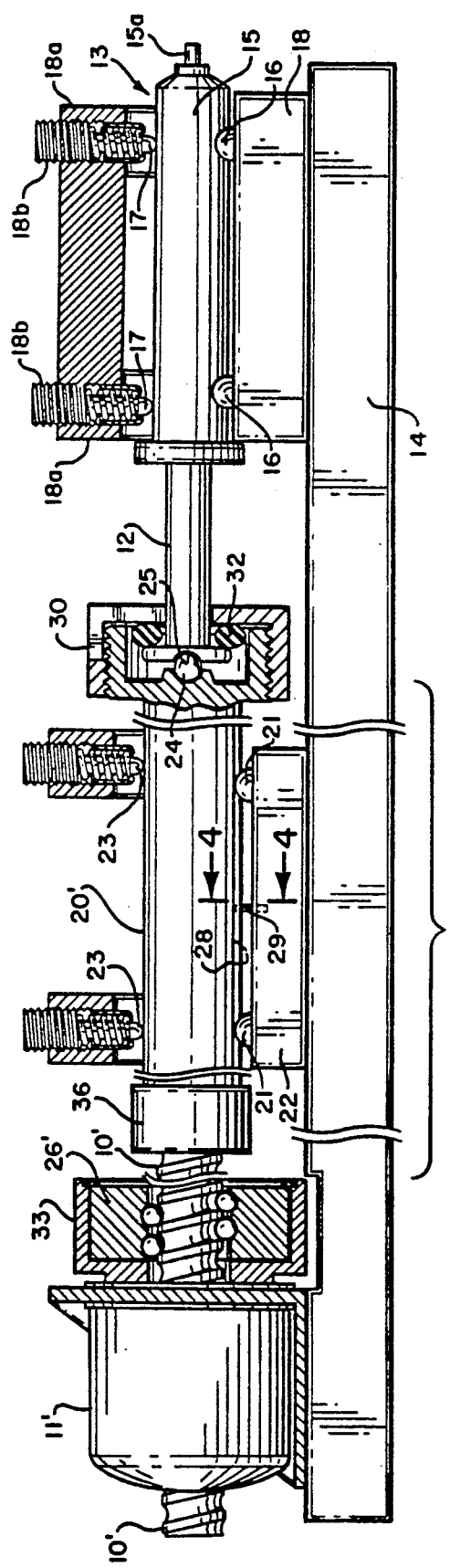
FIG. 6 illustrates another embodiment of the present invention.

FIG. 6 illustrates an alternative embodiment using a stepping motor 11' with a hollow motor shaft that allows the lead screw 10' to be advanced and retracted through it while a zero-backlash ball nut 26' is rotated. The ball nut 26' is secured to the hollow shaft of the stepping motor by a coupling member 33. A zero-backlash thrust bearing inside the motor housing is provided in commercially available units, but because thrust is dependent on motor bearings and such motor bearings generally have less load bearing capability than the ball nut 26', there is a compromise in the design of this embodiment with commercially available hollow-shaft stepping motors.

The flexible coupling 27 in the first embodiment shown in FIG. 1 next to the motor, is replaced in the embodiment of FIG. 6 by a coupling assembly 36 similar to the coupling assembly using the cup 30 and shown at the other end of the drive shaft. Another difference is that in the embodiment of FIG. 1, a support is preferably provided for the lead screw next to the flexible coupling in the form of a zero-backlash thrust bearing assembly 34 bolted to the bracket 35. A lock nut 34b on the lead screw on the other side of the bracket prevents axial motion of the lead screw in either direction. In the embodiment of FIG. 6, such zero-backlash thrust bearing assembly with lock nut is not required because the ball nut 26' is press fit into the motor coupling means 33 which prevents axial motion of the lead screw in either direction.

Figure 7A:
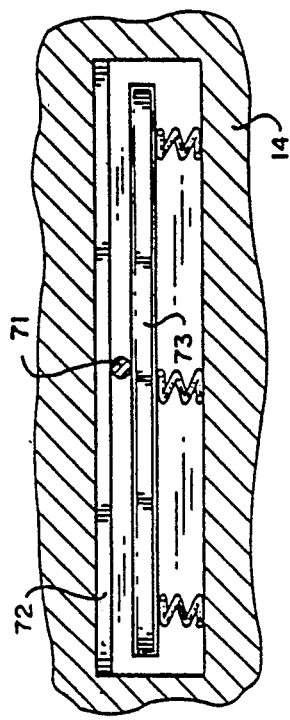
FIG. 7a is a cross section taken along a line 7a—7a in FIG. 7.
Figure 7:
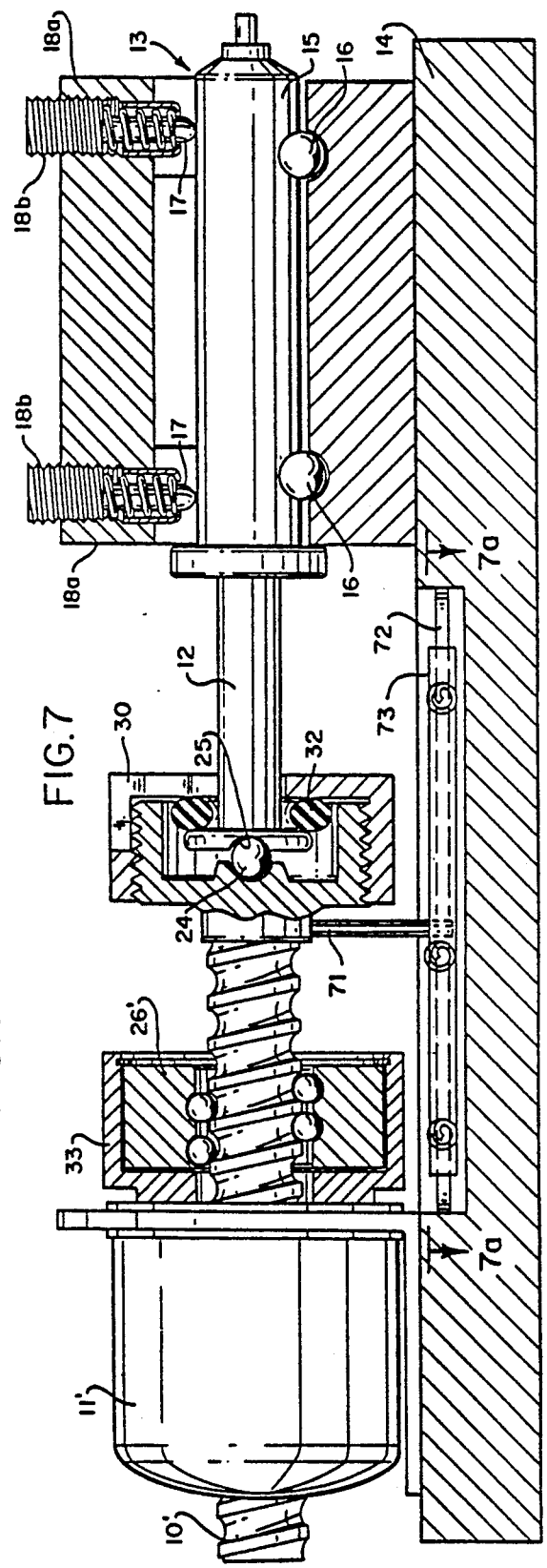
FIG. 7 illustrates yet another embodiment of the present invention.

In another embodiment shown in FIG. 7, the lead screw 10' is coupled directly to the end of the plunger 12 by a coupling assembly. The lead screw is prevented from rotating by a pin 71 extending perpendicularly from it and riding on a bar 72 which is parallel with the lead screw's rotational axis and mounted in a slot in the reference member 14, as shown in FIG. 7a. A spring-loaded bar 73 applies pressure against the perpendicular rod 71 so that it is always in contact with rod 72 during extraction or infusion. This is analogous to the arrangement shown in FIG. 4 to prevent the drive shaft 20 from rotating. It should be noted that another equivalent arrangement would use a ball attached to an arm perpendicular to the lead screw and resting on a precision flat surface parallel to the lead screw's rotational axis.

Although particular embodiments of the invention have been described and illustrated herein, it is recognized that modifications and variations may readily occur to those skilled in the art. For example, the stepper motor of FIG. 1 could be mounted in the gimbal mount of FIG. 5. The drive motor could then be coupled directly to the lead screw and eliminate the need for the coupling 27, the thrust bearing 34 and corresponding bracket 35. The advantage of mounting the drive motor on the gimbal is that misalignment errors would be accommodated. A disadvantage is the thrust load capability of the motor bearings and the gimbal mount.

Alternatively, the thrust bearing assembly could be replaced by the gimbal mount, thus eliminating the running in of the thrust bearing block during assembly. The disadvantage, again, is the thrust load capability of the gimbal.

The preferred embodiment of FIG. 1 has the following attributes: (1) It can apply the maximum force capable of the lead screw/nut assembly. The other embodiments using a hollow-shaft drive motor are limited to the thrust capability of the drive motor. While heavy duty zero-axial play bearings can be used in the construction of a hollow-shaft motor, it is not a readily available option. (2) It can accommodate off-axis loads due to misalignment of the plunger and drive shaft. (3) It facilitates easy replacement of syringes. Because the plunger seals wear out with usage, this is a necessary convenience. (4) It allows the use of readily available syringes. The intent of the design is to eliminate off-axis forces, but still accommodate the errors in alignment without having to rely on extraordinary measures to make the alignment errors as small as possible. The embodiment of FIG. 7 would be preferred over that of FIG. 1 and that of FIG. 6 if motors capable of high axial loads were available. It allows a simpler and more compact design. However, it would still not handle off-axis forces as well as the embodiments of FIG. 1 and FIG. 6.

We claim:

1. A syringe pump comprising:
a syringe having a barrel with an axis and a plunger having an end extending outside of said barrel and having an axis coaxially aligned with said barrel axis,
a reference member,
a motor supported by said reference member,
a drive shaft coaxial with said motor for imparting translational motion of said plunger in said barrel, said drive shaft having an axis coaxially aligned with said axis of said barrel,
means for coaxially coupling said drive shaft to the outside end of said plunger,
a lead screw coaxially aligned with said drive shaft having a zero-backlash ball nut for producing translational motion of said drive shaft along said axis of said drive shaft, said drive shaft being coupled to said plunger with its axis aligned with said axis of said drive shaft,
means for kinematically supporting said barrel of said syringe on said reference member and constraining said barrel against translational and rotational motion while said plunger undergoes translation motion in response to translation motion of said drive shaft produced by said motor through said lead screw and zero-backlash ball nut, and
means for kinematically supporting said drive shaft on said reference member and constraining said drive shaft against translational and rotational motion except for translational motion along its axis produced by said motor through said lead screw and zero-backlash ball nut.

2. A syringe pump comprising:
a syringe having a barrel with an axis and a plunger having an end extending outside of said barrel and having an axis coaxially aligned with said barrel axis;
a reference member;
a motor supported by said reference member;
a drive shaft coaxial with said motor for imparting translational motion of said plunger in said barrel, said drive shaft having an axis coaxially aligned with said axis of said barrel;
means for coaxially coupling said drive shaft to the outside end of said plunger;
a lead screw coaxially aligned with said drive shaft having a zero-backlash ball nut for producing translational motion of said drive shaft along said axis of said drive shaft, said drive shaft being coupled to said plunger with its axis aligned with said axis of said drive shaft;
means for kinematically supporting said barrel of said syringe on said reference member and constraining said barrel against translational and rotational motion while said plunger undergoes translation motion in response to translation motion of said drive shaft produced by said motor through said lead screw and zero-backlash ball nut, and
means for kinematically supporting said drive shaft on said reference member and constraining said drive shaft against translational and rotational motion except for translational motion along its axis produced by said motor through said lead screw and zero-backlash ball nut;
said means for kinematically supporting said drive shaft comprising a first pair and a second pair of bearing balls affixed to said reference member, each pair being spaced apart transversely for support of said drive shaft on said reference member, said first and second pair of bearing balls being spaced apart along the length of said drive shaft, and a pair of resilient clamping means, one directly over the axis of said drive shaft at the location of said first pair of bearing balls and one directly over the axis of said drive shaft at the location of said second pair of bearing balls.

3. A syringe pump as defined in claim 2 wherein each resilient clamping means is positioned at a respective location over one of said first and second pair of bearing balls in a plane perpendicular to said reference member and passing through the respective center of said one of said first and second pair of bearing balls.

4. A syringe pump as defined in claim 2 wherein said means for kinematically supporting said barrel of said syringe on said reference member comprises:

a first pair and a second pair of fixed balls, each pair being spaced apart along the length of said barrel for support of said barrel on said reference member, and a pair of resilient clamping means, one directly over the axis of said barrel at the location of said first pair of fixed balls and one directly over the axis of said barrel at the location of said second pair of fixed balls.

5. A syringe pump as defined in claim 4 wherein each resilient clamping means is positioned at a respective location over one of said first and second pair of fixed balls in a plane perpendicular to said reference member and passing through the respective center of said one of said first and second pair of fixed balls.

6. A syringe pump as defined in claim 5 wherein said drive shaft is hollow to allow rotational and relative translational motion of said lead screw within said hollow drive shaft, including means for coaxially coupling said motor to said lead screw to impart rotational motion thereto in response to rotational motion of said motor, and means for connecting said zero-backlash ball nut in a fixed relationship to said drive shaft to impart translational motion of said drive shaft in response to rotational motion of said lead screw which is in turn rotated by said motor.

7. A syringe pump as defined in claim 6 wherein said means for coaxially coupling said motor to said lead screw is comprised of a flexible coupling to provide tolerance in coaxial alignment of said motor and said lead screw.

8. A syringe pump as defined in claim 7 comprising a thrust bearing support for said lead screw on said reference member between said flexible coupling and said zero-backlash ball nut.

9. A syringe pump as defined in claim 2 wherein said motor has a hollow shaft to allow translational motion of said lead screw through said hollow shaft of said motor including means for coupling said motor to said zero-backlash ball nut to impart rotational motion thereto in direct response to rotational motion of said motor, and means for coaxially coupling said lead screw to said drive shaft, whereby translational motion is imparted to said drive shaft in response to rotational motion of said motor.

10. A syringe pump for delivering precise, minute quantities of a liquid with repeatable precision from a syringe of the type having a barrel and a plunger in the barrel, the barrel and the plunger having coaxially aligned axes; the pump comprising:

a reference member for supporting said pump;

a motor secured to said reference member and having an axis of motion that is coaxial with said barrel and plunger axes;

means coupling said motor to said plunger; and a first kinematic support supporting said coupling means on said reference member and permitting motion of said coupling means and said plunger only along the axes of said plunger and said barrel;

wherein said coupling means comprises a drive shaft and wherein said first kinematic support comprises a first pair and a second pair of bearing balls affixed to said reference member, each pair being spaced apart transversely for support of said drive shaft on said reference member, said first and second pair of bearing balls being spaced apart along the length of said drive shaft, and a pair of resilient clamping means, one directly over the axis of said drive shaft at the location of said first pair of bearing balls and one directly over the axis of said drive shaft at the location of said second pair of bearing balls.

11. The syringe pump recited in claim 10 further comprising a second kinematic support supporting said barrel on said reference member and constraining said barrel against motion during motion of said coupling means and said plunger.

12. The syringe pump recited in claim 11 wherein said second kinematic support comprises:

a first pair and a second pair of fixed balls, each pair being spaced apart along the length of said barrel for support of said barrel on said reference member, and a pair of resilient clamping means, one directly over the axis of said barrel at the location of said first pair of fixed balls and one directly over the axis of said barrel at the location of said second pair of fixed balls.

* * * * *